(12) United States Patent
Pyun et al.

(10) Patent No.: US 11,000,183 B2
(45) Date of Patent: May 11, 2021

(54) LASER-INDUCED BREAKDOWN SPECTROSCOPE AND MEDICAL DIAGNOSTIC DEVICE USING THE SAME

(71) Applicant: KOREA INSTITUTE OF MACHINERY & MATERIALS, Daejeon (KR)

(72) Inventors: Sung Hyun Pyun, Daejeon (KR); Dae-hoon Lee, Daejeon (KR); YoungHoon Song, Daejeon (KR); Kwan-Tae Kim, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 868 days.

(21) Appl. No.: 15/314,566

(22) PCT Filed: Mar. 20, 2015

(86) PCT No.: PCT/KR2015/002719
§ 371 (c)(1),
(2) Date: Nov. 29, 2016

(87) PCT Pub. No.: WO2015/182860
PCT Pub. Date: Dec. 3, 2015

(65) Prior Publication Data
US 2017/0196444 A1   Jul. 13, 2017

(30) Foreign Application Priority Data

May 30, 2014  (KR) .................. 10-2014-0066385
Jul. 11, 2014  (KR) .................. 10-2014-0087451

(51) Int. Cl.
*A61B 1/05* (2006.01)
*A61B 1/06* (2006.01)
(Continued)

(52) U.S. Cl.
CPC .......... *A61B 1/051* (2013.01); *A61B 1/00091* (2013.01); *A61B 1/00094* (2013.01);
(Continued)

(58) Field of Classification Search
CPC . A61B 1/051; A61B 1/00091; A61B 1/00094; A61B 1/00096; A61B 1/015;
(Continued)

(56) References Cited

U.S. PATENT DOCUMENTS 5,847,825 A * 12/1998 Alexander ........... G01N 21/718
                                                    356/318
6,069,695 A    5/2000 Rohr et al.
(Continued)

FOREIGN PATENT DOCUMENTS

JP          09201328       8/1997
JP          2002-017657    1/2002
(Continued)

*Primary Examiner* — Timothy J Neal
*Assistant Examiner* — William B Chou
(74) *Attorney, Agent, or Firm* — Lex IP Meister, PLLC

(57) ABSTRACT

A laser-induced breakdown spectroscope according to an exemplary embodiment of the present invention includes: a laser head which emits a laser beam; a focusing lens which focuses the laser beam on a target specimen; a plasma reactor unit which amplifies first plasma, which is generated on the target specimen positioned at a focal point of the laser beam passing through the focusing lens, by controlling electron density and electron energy of the first plasma; a collection lens which focuses second plasma amplified by the plasma reactor unit; and a spectrophotometer which analyzes the second plasma focused by the collection lens.

7 Claims, 6 Drawing Sheets

(51) Int. Cl.
*A61B 1/07* (2006.01)
*G01J 3/28* (2006.01)
*G01N 21/39* (2006.01)
*G01J 3/443* (2006.01)
*G01N 21/73* (2006.01)
*G02B 23/26* (2006.01)
*A61B 5/00* (2006.01)
*A61B 1/00* (2006.01)
*A61B 1/018* (2006.01)
*A61B 1/015* (2006.01)
*G01N 21/31* (2006.01)
*G01N 21/71* (2006.01)
*G02B 23/24* (2006.01)
*H04N 5/225* (2006.01)

(52) U.S. Cl.
CPC .......... *A61B 1/00096* (2013.01); *A61B 1/015* (2013.01); *A61B 1/018* (2013.01); *A61B 1/0669* (2013.01); *A61B 1/07* (2013.01); *A61B 5/0075* (2013.01); *A61B 5/6847* (2013.01); *G01J 3/28* (2013.01); *G01J 3/443* (2013.01); *G01N 21/31* (2013.01); *G01N 21/39* (2013.01); *G01N 21/718* (2013.01); *G01N 21/73* (2013.01); *G02B 23/2469* (2013.01); *G02B 23/2484* (2013.01); *G02B 23/26* (2013.01); *H04N 5/2256* (2013.01); *A61B 2505/05* (2013.01); *A61B 2562/0233* (2013.01); *G01N 2201/06113* (2013.01); *H04N 2005/2255* (2013.01)

(58) Field of Classification Search
CPC ......... A61B 1/018; A61B 1/0669; A61B 1/07; A61B 5/0075; A61B 5/6847; A61B 2505/05; A61B 2562/0233
See application file for complete search history.

(56) References Cited

U.S. PATENT DOCUMENTS

| | | | |
|---|---|---|---|
| 6,565,505 B2 | 5/2003 | Ishibiki | |
| 7,060,026 B2 | 6/2006 | Ishibiki | |
| 8,537,203 B2 * | 9/2013 | Seibel | A61B 1/0008 |
| | | | 348/45 |
| 9,161,684 B2 * | 10/2015 | Seibel | A61B 1/0008 |
| 2001/0043330 A1 * | 11/2001 | Jung | G01J 1/06 |
| | | | 356/419 |
| 2003/0076497 A1 * | 4/2003 | Wolf | G01N 21/211 |
| | | | 356/369 |
| 2005/0234436 A1 * | 10/2005 | Baxter | A61B 18/1492 |
| | | | 606/14 |
| 2009/0299354 A1 * | 12/2009 | Melsky | A61B 18/245 |
| | | | 606/16 |
| 2011/0224519 A1 | 9/2011 | Adachi et al. | |
| 2015/0265143 A1 | 9/2015 | Yoon | |

FOREIGN PATENT DOCUMENTS

| | | |
|---|---|---|
| JP | 2005-168606 | 6/2005 |
| JP | 2006-130183 | 5/2006 |
| JP | 2011-185842 | 9/2011 |
| KR | 10-2000-0022345 | 4/2000 |
| KR | 10-1150350 | 6/2012 |

* cited by examiner

LASER-INDUCED BREAKDOWN SPECTROSCOPE AND MEDICAL DIAGNOSTIC DEVICE USING THE SAME

TECHNICAL FIELD

The present invention relates to a laser-induced breakdown spectroscope, and more particularly, to a laser-induced breakdown spectroscope using a plasma reactor, which improves sensitivity of a signal by using a plasma reactor, and a medical diagnostic device using laser-induced breakdown spectroscopy, which analyzes a diagnosis target in real time.

BACKGROUND ART

General laser-induced breakdown spectroscopy (LIBS) is a type of atomic emission spectroscopy, and is similar to inductively coupled plasma (ICP).

In the laser-induced breakdown spectroscopy, when a high-output laser beam is focused on a target specimen, plasma, which emits bright light such as breakdown, is formed at a focal point, and a high temperature is maintained.

The target specimen is vaporized, atomized, and ionized in the plasma, and atoms and ions may be present in an excited state by absorbed energy.

When predetermined time has elapsed, the atoms and the ions in the excited state emit energy and return back to the ground state. In this case, the emitted energy shows inherent wavelengths in accordance with the type of element and the excited state.

By analyzing spectrums of the wavelengths by using a spectrophotometer (UV-vis spectroscope), it is possible to qualitatively and quantitatively analyze the target specimen. Therefore, in the laser-induced breakdown spectroscopy, it is important to precisely measure a plasma signal generated from the target specimen. Specifically, analysis sensitivity in respect to the generated plasma signal is important.

That is, the developmental direction of the laser-induced breakdown spectroscopy is to increase a detection limit for each element in respect to the target specimen while minimizing damage to the target specimen by using a smaller amount of laser energy.

The plasma signal, which is generated from the target specimen as the target specimen is subjected to laser, is maintained for several microseconds (μs), and then immediately disappears. Therefore, under a condition that requires high sensitivity or a condition in which it is difficult to receive a signal, the laser-induced breakdown spectroscopy may emit laser twice or several times at several nanosecond (ns) to microsecond (μs) time intervals.

Meanwhile, since the aforementioned laser-induced breakdown spectroscopy may analyze element components of a target material in real time, the laser-induced breakdown spectroscopy is required to be utilized in a medical field such as a disease diagnosis.

As an example, recently, auxiliary imaging devices, such as magnetic resonance imaging (MRI) and computed tomography (CT), are utilized for a cancer diagnosis. However, the imaging devices cannot provide chemical information about tissue, and merely provide auxiliary information about shapes of tissue, and as a result, the cancer diagnosis depends on a physician's experiential judgement.

A biopsy, which is performed for two hours to several days, is required for a perfect cancer diagnosis, and even though whether the tissue excised from the body has cancer is determined, it is impossible to recognize how the cancer is spread in the tissue present in the body. Therefore, it is very difficult to calculate a range of the body tissue to be excised and removed, and a laparotomy is required for the purpose of the treatment.

Therefore, it is necessary to perform the cancer diagnosis on the body tissue in real time, and determine whether the tissue has a malignant or benign disease while rarely damaging the body tissue. That is, it is necessary to perform the cancer diagnosis without excessively excising or removing normal tissues from the body tissues.

DISCLOSURE

Technical Problem

The present invention has been made in an effort to provide a laser-induced breakdown spectroscope using a plasma reactor which increases a detection limit for each element by increasing intensity of a plasma generated on an analysis target specimen, or extending a duration time of the generated plasma.

The present invention has also been made in an effort to provide a medical diagnostic device using laser-induced breakdown spectroscopy, which analyzes constituent elements of a diagnosis target in real time.

Technical Solution

That is, an object of the present invention is to provide a medical diagnostic device in which a laser-induced breakdown spectroscopy unit and an endoscopy unit are integrated, and to provide a medical diagnostic device which compares ratios of the constituent elements of a tissue having a disease (e.g., cancer) with ratios of constituent elements of a normal tissue (e.g., a ratio of Na/K elements, a ratio of Ca/Na elements, etc.), carries out the diagnosis for a disease (e.g., cancer) in real time based on the difference, approaches a portion where a typical endoscope may approach, and analyzes the element of the diagnosis target.

The present invention has also been made in an effort to provide a medical diagnostic device which analyzes; in real time, constituent elements of the diagnosis target even though the diagnosis target is placed at the exterior of the body.

An exemplary embodiment of the present invention provides a laser-induced breakdown spectroscope including: a laser head which emits a laser beam; a focusing lens which focuses the laser beam on a target specimen; a plasma reactor unit which amplifies a first plasma, which is generated on the target specimen positioned at a focal point of the laser beam passing through the focusing lens, by controlling electron density and electron energy of the first plasma; a collection lens which focuses a second plasma amplified by the plasma reactor unit; and a spectrophotometer which analyzes the second plasma focused by the collection lens.

The plasma reactor unit may convert the first plasma into the second plasma through a dielectric barrier discharge.

The plasma reactor unit may include: a housing which is disposed on the target specimen and made of a dielectric substance; and a pair of first electrodes and a pair of second electrodes which are provided at an outer circumference of the housing, and generates the second plasma in the housing through the dielectric barrier discharge when driving voltage is applied.

The plasma reactor unit may further include a gas supply unit which supplies discharge gas into the housing.

The housing may be made of quart, and may have a cylindrical shape.

The housing may be installed on a specimen support unit which supports the target specimen, and the housing may accommodate the target specimen.

Another exemplary embodiment of the present invention provides a medical diagnostic device including: a laser-induced breakdown spectroscopy unit which includes a laser guide bundle that is connected to a laser head so as to emit a laser beam to a diagnosis target, and a spectroscopy guide bundle that is connected to a spectrophotometer so as to receive a plasma signal generated from the diagnosis target; and a probe which is provided with the laser guide bundle and the spectroscopy guide bundle, and disposed to approach the diagnosis target.

The laser guide bundle may include: a first optical fiber which is connected to the laser head; and a focusing lens which is disposed on the probe at the front of the first optical fiber so as to focus the laser beam, which is transmitted to the first optical fiber, on the diagnosis target.

The spectroscopy guide bundle may include: a second optical fiber which is connected to the spectrophotometer; and a collection lens which is disposed on the probe at the front of the second optical fiber so as to receive the plasma signal generated from the diagnosis target, and send the plasma signal to the second optical fiber.

The focusing lens and the collection lens may be disposed to be coplanar with each other at an end portion of the probe.

The laser beam may be a nanosecond pulse laser beam or a femtosecond pulse laser beam.

The medical diagnostic device may further include a plasma reactor unit which amplifies the plasma signal, which is generated from the diagnosis target, by controlling electron density and electron energy of the plasma signal, in which the plasma signal amplified by the plasma reactor unit is transmitted to the spectroscopy guide bundle.

The medical diagnostic device may further include an endoscopy unit which includes an insertion tube that approaches the diagnosis target, a bending member that is provided at one side of the insertion tube and connects the insertion tube and the probe, and a controller which is provided at the other side of the insertion tube.

The endoscopy unit may further include a light guide bundle, and the light guide bundle may include: a third optical fiber which is connected to a light source; and a lens which is provided on the probe at the front of the third optical fiber.

The endoscopy unit may further include an image capturing unit, and the image capturing unit may include: an objective lens which is provided on the probe and captures an image of the diagnosis target a charge-coupled device (CCD) which is disposed at the rear of the objective lens, and digitalizes the image; and an image display unit which is connected to the charge-coupled device and implements an image with the digital signal.

The endoscopy unit may further include an air/water supply unit, and the air/water supply unit may include: an air/water nozzle which is provided on the probe, and sprays air or water to the diagnosis target; and an air/water pump which is connected to the air/water nozzle, and supplies air or water from the outside.

The endoscopy unit may further include an aspiration unit, and the aspiration unit may include: a removal/aspiration channel which is provided in the probe so as to remove a tissue of the diagnosis target, or disposed at the periphery of the diagnosis target; and an aspiration pump which is connected to the removal/aspiration channel, and aspirates the removed tissue or substances at the periphery of the diagnosis target.

Advantageous Effects

According to the exemplary embodiment of the present invention having the aforementioned configurations, the plasma reactor unit is provided on the target specimen, and the plasma reactor unit controls and amplifies the first plasma, which is generated on the target specimen by the laser beam, to the second plasma, such that it is possible to increase intensity of plasma generated on the target specimen, or to extend duration time of the plasma. Therefore, with the spectrophotometer, it is possible to increase a detection limit for each element of the target specimen.

According to the exemplary embodiment of the present invention, the laser-induced breakdown spectroscopy unit is coupled to the endoscopy unit or a separate laser-induced breakdown spectroscope is used, and as a result, it is possible to analyze the constituent element of the diagnosis target in real time by receiving the plasma signal generated from the diagnosis target in real time.

In the exemplary embodiment, it is possible to diagnose a disease (e.g., cancer) in real time by analyzing the constituent element of the diagnosis target in real time, and by comparing ratios of the constituent element of the diagnosis target tissue (e.g., cancer tissue) with ratios of the constituent elements of a normal tissue.

In addition, in the exemplary embodiment, the probe directly approaches the diagnosis target while performing a diagnosis of a disease (e.g., cancer) and as a result, it is possible to analyze the substance of the diagnosis target, and to immediately remove the diagnosis target by using a high-output laser or a discharge without performing a laparotomy on a patient.

DESCRIPTION OF SYMBOLS

Figure 1:
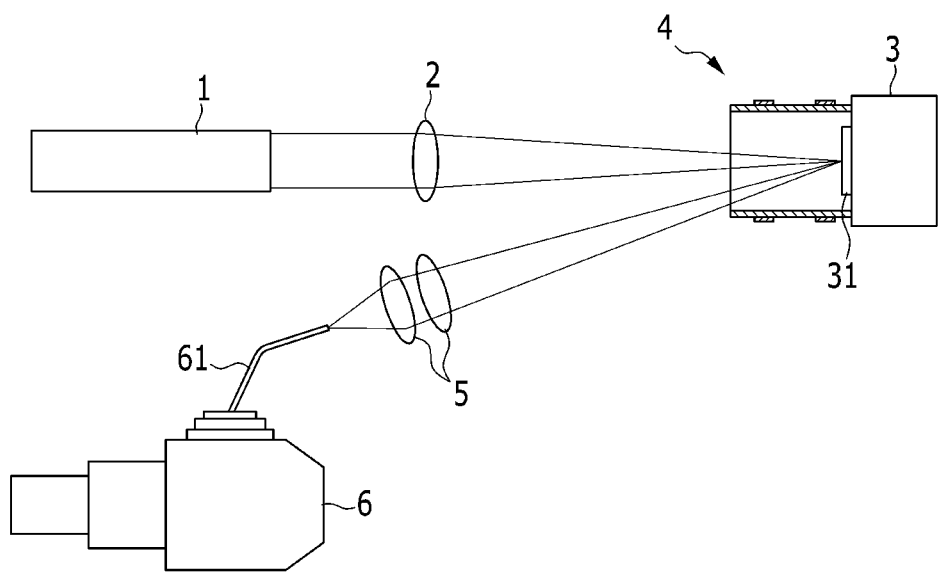
FIG. 1 is a configuration diagram of a laser-induced breakdown spectroscope according to an exemplary embodiment of the present invention.

| | |
|---|---|
| 1: Laser head | 2: Focusing lens |
| 3: Specimen support unit | 4: Plasma reactor unit |
| 5: Collection lens | 6: Spectrophotometer |
| 31: Target specimen | 41: First electrode |
| 42: Second electrode | 43: Housing |
| 44: Gas supply unit | 45: Port |
| 61: Optical fiber | G: Discharge gap |
| P1, P2: First, Second plasma | V: Driving voltage |
| 100: Endoscopy unit | |

-continued

| | |
|---|---|
| 200: Laser-induced breakdown spectroscopy unit | |
| 110: Insertion tube | 120: Bending member |
| 130: Probe | 140: Controller |
| 210: Laser guide bundle | |
| 220: Spectroscopy guide bundle | |
| 230: Light guide bundle | 240: Image capturing unit |
| 250: Air/water supply unit | 260: Aspiration unit |
| 211: Laser head | 212: First optical fiber |
| 213: Focusing lens | 221: Spectrophotometer |
| 222: Second optical fiber | 223: Collection lens |
| 231: Light source | 232: Third optical fiber |
| 233: Lens | 241: Objective lens |
| 242: Charge-coupled device (CCD) | 243: Image display unit |
| 251: Air/water pump | 252: Air/water nozzle |
| 261: Aspiration pump | |
| 262: Removal/aspiration channel | |

MODE FOR INVENTION

Hereinafter, the present invention will be described more fully hereinafter with reference to the accompanying drawings, in which example embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

FIG. 1 is a configuration diagram of a laser-induced breakdown spectroscope according to an exemplary embodiment of the present invention.

Referring to FIG. 1, a laser-induced breakdown spectroscope is a spectroscope using a plasma reactor, and includes a laser head 1, a focusing lens 2, a specimen support unit 3, a plasma reactor unit 4, collection lenses 5, and a spectrophotometer 6.

The laser head 1 is operated by electric power supplied from a non-illustrated laser power supply, and emits a laser beam having a pulse. The electric power may be supplied as AC or DC power. The focusing lens 2 focuses the laser beam, and applies the laser beam to a target specimen 31.

The specimen support unit 3 is configured to support the target specimen 31, and to be directed toward the focusing lens 2 and the collection lens 5. The specimen support unit 3 may be used when the target specimen 31 has a small size, and may not be used when a target specimen (not illustrated) has a larger size.

As illustrated, in a case in which the target specimen 31 has a small size, the target specimen 31 may be disposed on the specimen support unit 31, and the plasma reactor unit 4 may be installed on the specimen support unit 31 in a state in which the plasma reactor unit 4 accommodates the target specimen 31.

Although not illustrated, in a case in which the target specimen has a large size, the plasma reactor unit may be installed at an upper side at one side of the target specimen.

The laser beam is focused by the focusing lens 2, and applied to the target specimen 31, thereby generating a first plasma P1. That is, the laser beam generates the first plasma P1 while removing a small amount of mass from a surface of the target specimen 31 on which the laser beam is focused.

The first plasma P1 begins to be generated on the surface of the target specimen 31 at a high temperature (e.g., 30,000K or higher), and quickly expands. The first plasma P1 continuously emits light for an initial step (e.g., 200 to 300 ns or shorter) during a cooling process.

The plasma reactor unit 4 generates a second plasma P2 that is amplified by controlling electron density and electron energy of the first plasma P1 generated on the target specimen 31. After several microseconds (μs), electron lines having inherent wavelengths are emitted from the second plasma P2, and the plasma reactor unit 4 amplifies the emission of the electron lines by the generation of the second plasma P2. In this case, in order to increase the generated electron density and a temperature, discharge gas such as argon and helium may be additionally supplied into the plasma reactor unit 4.

The second plasma P2 is focused by the collection lens 5. That is, the collection lens 5 focuses the electron lines which are amplified and emitted. The electron lines, which are focused by the collection lens 5, that is, the wavelengths of the electron lines are inputted to the spectrophotometer 6 through an optical fiber 61.

The spectrophotometer 6 detects, measures, and analyzes the inputted wavelengths of the second plasma P2. Since the first plasma P1 is amplified to the second plasma P2, the wavelength of the second plasma P2, which is detected from the target specimen 31, may be more easily and precisely measured. That is, analysis sensitivity is improved for a signal of the second plasma P2.

Figure 2:
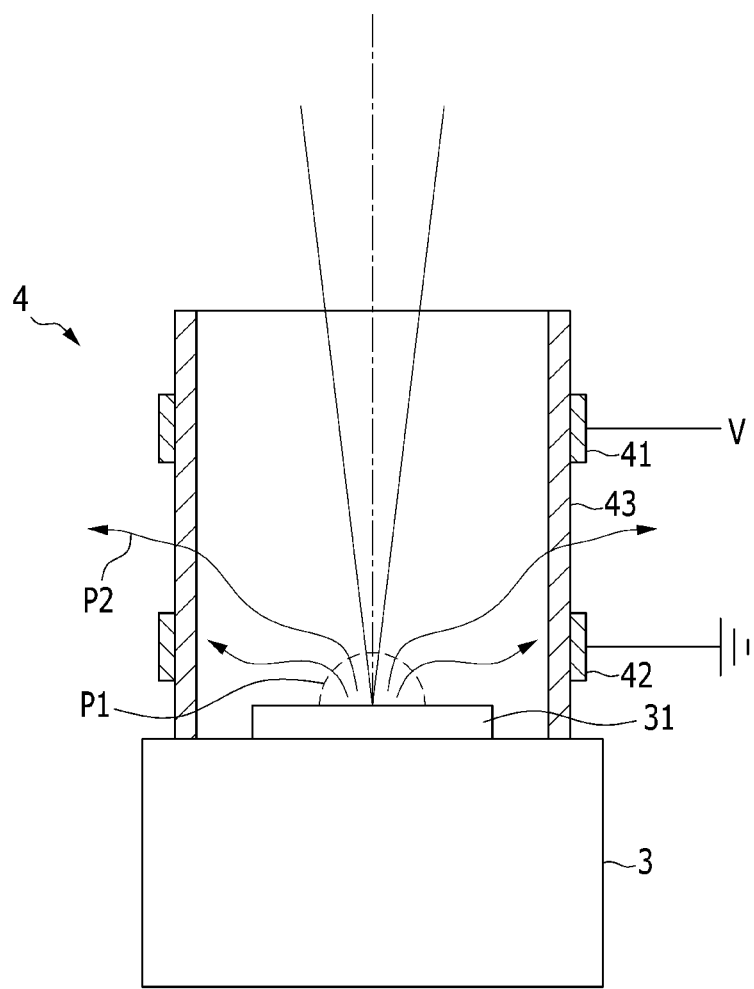
FIG. 2 is a view illustrating a state in which a plasma reactor unit is installed on a specimen support unit in FIG. 1 and plasma generated from a target specimen is amplified.

FIG. 2 is a view illustrating a state in which the plasma reactor unit is installed on the specimen support unit in FIG. 1 and the plasma generated from the target specimen is amplified. Referring to FIG. 2, the plasma reactor unit 4 is configured to control and amplify the first plasma P1 to the second plasma P2 through a dielectric barrier discharge.

The plasma reactor unit 4 is configured to generate the second plasma P2 by converting the first plasma P1, which is generated from the target specimen 31 by the laser beam, into the dielectric barrier discharge. Since the plasma reactor unit 4 uses the dielectric barrier discharge (DBD), the plasma reactor unit 4 may be operated with lower driving voltage V.

The plasma reactor unit 4 includes a housing 43 which is disposed on the specimen support unit 3, accommodates the target specimen 31, and is made of a dielectric substance, and a pair of first electrodes 41 and a pair of second electrodes 42 which are provided at an outer circumference of the housing 43 and generate the second plasma P2 through the dielectric barrier discharge.

In addition, the plasma reactor unit 4 may include a gas supply unit 44. The gas supply unit 44 may include a discharge gas supply tank, supply piping, and the like so as to additionally supply the discharge gas into the housing 43. In this case, a port 45, which is connected with the gas supply unit 44 and allows the discharge gas such as argon, helium, and air to be supplied into the housing 43, may be provided at one side of the housing 43. The port 45 may include a passageway which connects the gas supply unit 44 with an interior of the housing 43.

The housing 43 may be made of a dielectric substance, for example, quartz, formed in a cylindrical shape, and disposed at one side of the specimen support unit 3. In order to radiate heat, the housing 43 is formed to be opened at a side through which the laser beam enters and which is opposite to the specimen support unit 3.

As illustrated in FIG. 2, the target specimen 31 having a small size is disposed in the housing 43. A discharge gap G is defined between the first electrode 41 and the second electrode 42. Although not illustrated, in a case in which the target specimen has a large size, the housing may be disposed at an upper side at one side of the target specimen.

When the laser beam is emitted from the laser head 1 in this state, the laser beam, which is emitted to the target specimen 31 through the focusing lens 2, generates the first plasma P1 on the target specimen 31.

Further, when the driving voltage V is applied to the first electrode 41 and the second electrode 42 is grounded, wall charge is formed on the housing 43 corresponding to the discharge gap G, thereby generating the dielectric barrier discharge.

With the dielectric barrier discharge, the first plasma P1, which is generated on the target specimen 31 positioned in the housing 43, is amplified and converted into the second plasma P2. That is, the second plasma P2 is formed by controlling electron density and electron energy of the first plasma P1.

The low voltage operation according to the dielectric barrier discharge reduces energy required for the plasma reactor unit 4, and reduces a burden of a power source by decreasing the driving voltage V required to generate the second plasma P2.

In addition, various chemical species, that is, vibrationally excited species, ions, and radicals are generated by the first plasma P1 generated by the laser beam In many instances, the chemical species are maintained for several nanoseconds to several microseconds, and the lifetime of the chemical species included in the first plasma P1 is extended by the second plasma P2 of the plasma reactor unit 4, and as a result, chemical species may be involved in accordance with a time scale of a desired chemical reaction.

Although not illustrated, the plasma reactor unit may be provided with the first electrode, and grounds the specimen support unit spaced apart at the discharge gap, thereby implementing the dielectric barrier discharge by forming the wall charge in the housing which is positioned between the first electrode and the specimen support unit.

Meanwhile, the aforementioned laser-induced breakdown spectroscope may be utilized to diagnose diseases such as cancer in body tissue, and hereinafter, a medical diagnostic device using the laser-induced breakdown spectroscopy will be described.

Figure 3:
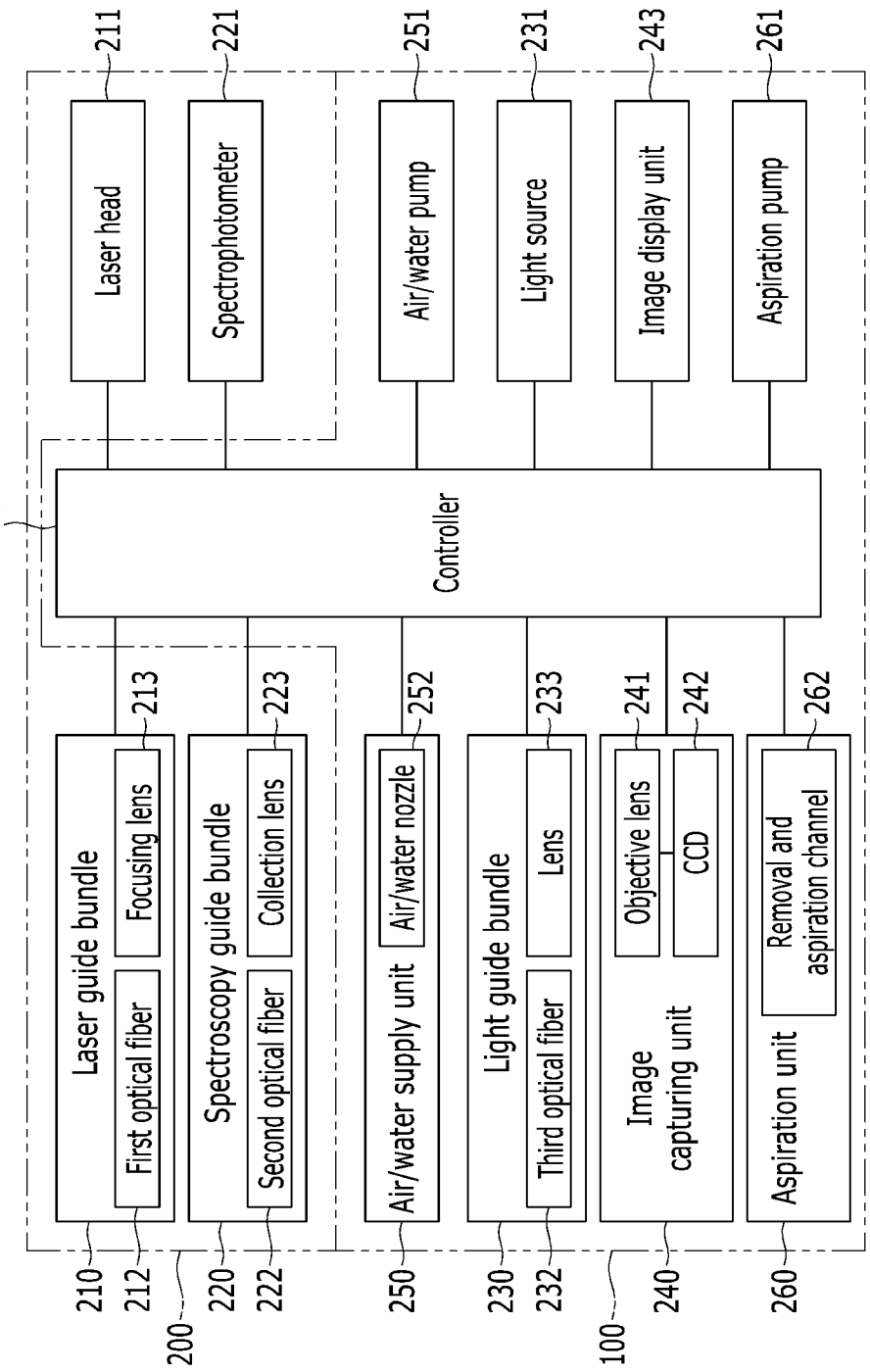
FIG. 3 is a block diagram illustrating a configuration of a medical diagnostic device according to the exemplary embodiment of the present invention.
Figure 4:
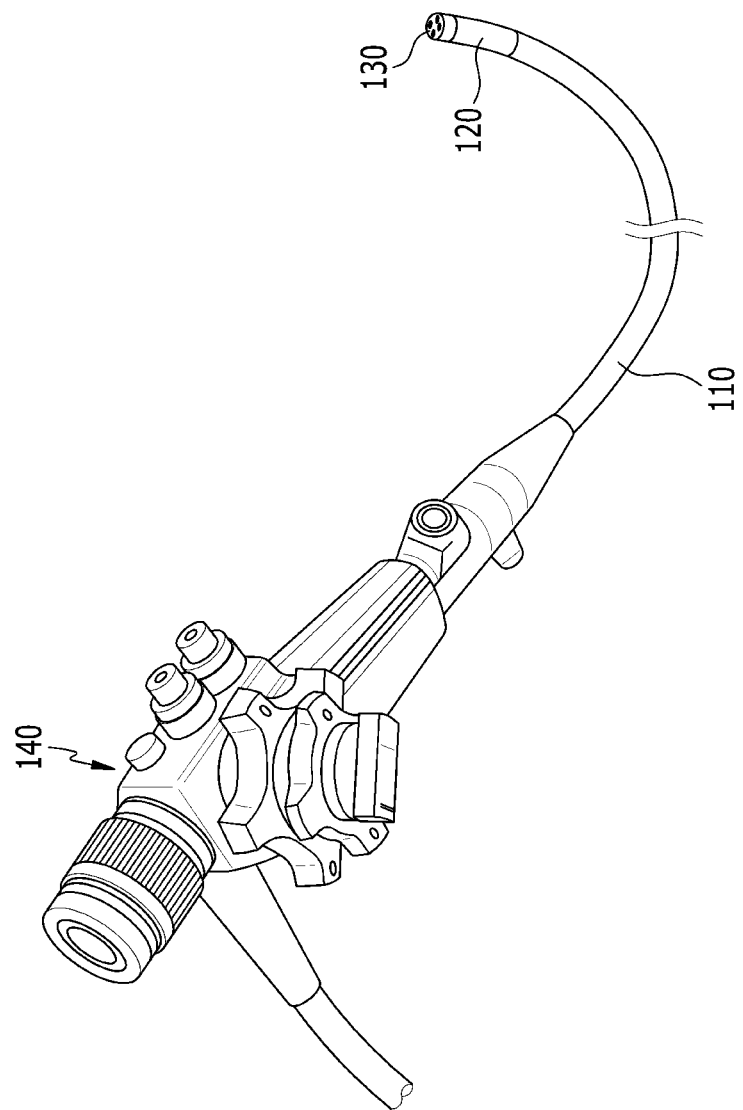
FIG. 4 is a perspective view illustrating a state in which an insertion tube is connected to a controller in FIG. 1.

FIG. 3 is a block diagram illustrating a configuration of a medical diagnostic device according to the exemplary embodiment of the present invention, and FIG. 4 is a perspective view illustrating a state in which an insertion tube is connected to a controller in FIG. 3.

Referring to FIGS. 3 and 4, the medical diagnostic device according to the exemplary embodiment includes an endoscopy unit 100 and a laser-induced breakdown spectroscopy unit 200. That is, the medical diagnostic device is configured to approach a diagnosis target by using the endoscopy unit 100, and emit a laser beam to the diagnosis target and analyze the diagnosis target based on a plasma signal generated from the diagnosis target by using the laser-induced breakdown spectroscopy unit 200.

The endoscopy unit 100 includes an insertion tube 110 which may approach the diagnosis target, a bending member 120 which is provided at one side of the insertion tube 110, and a probe 130 which is connected to the bending member 120. The endoscopy unit 100 further includes a controller 140 connected to the other side of the insertion tube 110.

The insertion tube 110 may be inserted into a patient's body, or may approach an exterior of the body. That is, the insertion tube 110 is inserted into the body or moved to the exterior of the body, thereby enabling the probe 130 to approach the diagnosis target.

Although not specifically illustrated, a bending member used for a publicly known endoscope may be used. For example, the bending member may have a plurality of chains which is connected in a ring shape from the controller to the probe, such that when the controller is rotated, the probe may be bent in a direction identical to a rotation direction of the controller. The bending member is bent at 90 degrees or greater in all directions including forward, rearward, leftward, and rightward directions, and as a result, it is possible to observe the diagnosis target by using the probe in all the directions with the combined bending member.

The probe 130 is connected to the bending member 120 so as to define a tip portion of the endoscopy unit 100, and when the insertion tube 110 is inserted into the body or moved to the exterior of the body, the probe 130 directly approaches the diagnosis target.

Therefore, the probe 130 may be provided with constituent elements that diagnose the diagnosis target, and the controller 140 may supply necessary things to the constituent elements of the probe 130 or may obtain necessary things from the constituent elements of the probe 130.

The laser-induced breakdown spectroscopy unit 200 includes a laser guide bundle 210 which emits the laser beam to the diagnosis target, and a spectroscopy guide bundle 220 which receives the plasma signal generated from the diagnosis target.

The laser guide bundle 210 and the spectroscopy guide bundle 220 are provided on the probe 130, and connected to a laser head 211 and a spectrophotometer 221, respectively, through the insertion tube 110. In addition, the laser guide bundle 210 and the spectroscopy guide bundle 220 are connected to the controller 140 through the insertion tube 110.

With the operation of the controller 140, the laser guide bundle 210 and the spectroscopy guide bundle 220 approach the diagnosis target by the probe 130 and the bending member 120, and face the diagnosis target at various angles.

The laser beam generated from the laser head 211 may be a nanosecond pulse laser beam or a femtosecond pulse laser beam. The nanosecond pulse laser having pulse time of several nanoseconds ($10^{-9}$ seconds) obtains a plasma signal by damaging a part of a hard solid specimen such as a mineral (e.g., several micrograms), and may heat and damage a biological tissue when the biological tissue containing a large amount of water is analyzed. Therefore, an Nd:YAG nanosecond pulse laser, which is a nanosecond pulse laser, may be utilized.

In addition, the femtosecond pulse laser has much shorter pulse time (several femtoseconds ($10^{-15}$ seconds)) than the nanosecond pulse laser while providing peak power identical to that of the nanosecond pulse laser, thereby reducing energy to be transferred to the diagnosis target. Therefore, the femtosecond pulse laser does not unnecessarily heat or damage the diagnosis target.

Figure 5:
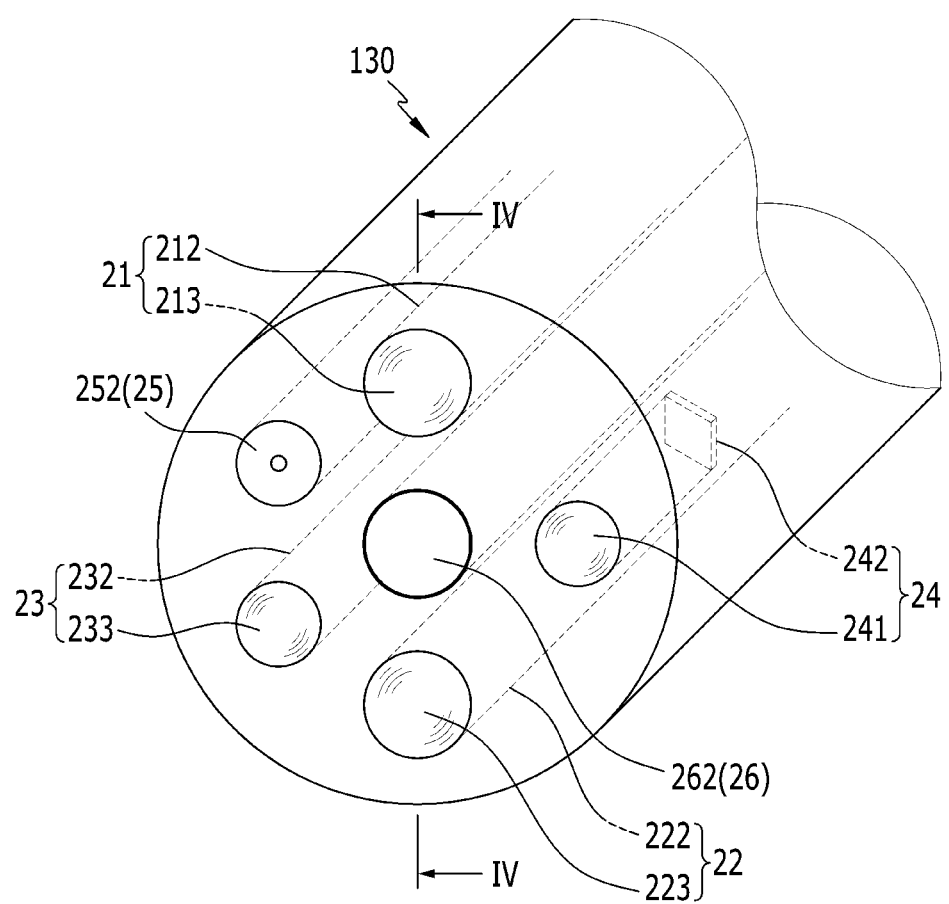
FIG. 5 is a partial perspective view of a probe provided at an end of the insertion tube.
Figure 6:
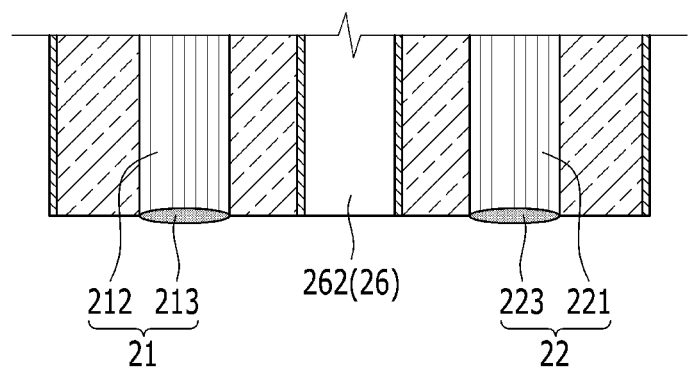
FIG. 6 is a cross-sectional view taken along line VI-VI in FIG. 5.

FIG. 5 is a partial perspective view of the probe provided at the end of the insertion tube, and FIG. 6 is a cross-sectional view taken along line VI-VI in FIG. 5. Referring to FIGS. 5 and 6, the laser guide bundle 210 includes a first optical fiber 212 which is connected to the laser head 211, and a focusing lens 213 which is provided on the probe 130 at the front of the first optical fiber 212.

The focusing lens 213 focuses the laser, which is generated from the laser head 211 and transmitted through the first optical fiber 212, on the diagnosis target. The high-output pulse laser, which is focused on the diagnosis target by the focusing lens 213, strikes the diagnosis target, thereby generating plasma.

The spectroscopy guide bundle 220 includes a second optical fiber 222 which is connected to the spectrophotometer 221, and a collection lens 223 which provided on the probe 130 at the front of the second optical fiber 222.

The collection lens 223 receives the plasma signal generated from the diagnosis target. The plasma signal, which is received by the collection lens 223, is sent to the spectrophotometer 221 through the second optical fiber 222.

The plasma signal, which is generated by the high-output pulse laser focused by the focusing lens 213, has various inherent wavelengths in accordance with the type of element that constitutes the diagnosis target. The spectrophotometer 221 displays signal intensity, through a graph, in accordance with the wavelength of the plasma signal.

Therefore, an inspector may determine whether the diagnosis target is abnormal by comparing an intensity graph according to the wavelength of the plasma signal with an intensity graph according to a wavelength of a plasma signal of an normal diagnosis target, and may identify which state the diagnosis target is in, that is, which disease or cancer the diagnosis target has.

That is, by using the fact that proportions of particular elements (e.g., a ratio of Na/K elements, a ratio of Ca/Na elements, etc.), among the elements that constitute the tissue, are changed particularly in accordance with the types of various diseases including cancer, it is possible to determine whether particular diseases or cancer are in progress.

Although not illustrated separately, in the exemplary embodiment of the present invention, the medical diagnostic device may further include a plasma reactor unit which amplifies the plasma signal generated from the diagnosis target.

In this case, the plasma reactor unit may amplify the plasma signal by controlling electron density and electron energy of the plasma signal generated from the diagnosis target, and because the plasma reactor unit corresponds to the aforementioned plasma reactor unit 4 illustrated in FIGS. 1 and 2, a detailed description thereof will be omitted.

The plasma signal, which is amplified by the plasma reactor unit, is transmitted to the spectroscopy guide bundle. In more detail, the plasma signal, which is amplified by the plasma reactor unit, is received by the collection lens 223, and transmitted to the spectrophotometer 221 through the second optical fiber 222.

As illustrated in FIG. 6, the focusing lens 213 and the collection lens 223 are disposed to be coplanar with each other at the end portion of the probe 130. FIG. 6 illustrates an example.

Although not illustrated, for the purpose of sensitivity of light receiving portions of the focusing lens and the collection lens, the end portion of the probe may be formed to be concave inward. In this case, the focusing lens and the collection lens are not coplanar with each other at the end portion of the probe, and optical paths, which are perpendicular to the focusing lens and the collection lens, respectively, intersect at a point where a material of the diagnosis target becomes plasma.

Therefore, the focusing lens 213 may focus the high-output pulse laser on the diagnosis target, and the collection lens 223 may effectively receive the plasma signal generated in this case.

Referring back to FIGS. 3 and 4, the endoscopy unit 100 may further include a light guide bundle 230. The light guide bundle 230 includes a third optical fiber 232 which is connected to a light source 231, and a lens 233 which m is disposed on the probe 130 at the front of the third optical fiber 232.

The third optical fiber 232 effectively transmits light of the light source 231 to the diagnosis target in order to capture an image of the diagnosis target, and to this end, the lens 233 is provided at the front of the third optical fiber 232. Although not illustrated, a lens is also provided at the opposite side of the third optical fiber 232.

Although not illustrated, the light guide bundle may not be provided in a laser-induced breakdown spectroscopy endoscope which is used in a situation in which a probe is not inserted into the body and an exterior of the body exposed to a sufficiently bright environment is the diagnosis target.

The endoscopy unit 100 may further include an image capturing unit 240. The image capturing unit 240 includes an objective lens 241 which is provided on the probe 130 and captures the image of the diagnosis target, a charge-coupled device (CCD) 242 which is disposed at the rear of the objective lens 241 and digitalizes the image, and an image display unit 243 which is connected to the charge-coupled device 242 through a cable and implements an image with the digital signal.

Several thousands of photosites, that is, pixels, which detect light, are arranged on a surface of the charge-coupled device (CCD) 242. The CCD 242 detects light which is emitted through the light guide bundle 230 and reflected by the diagnosis target.

The CCD 242 is positioned on the probe 130 immediately behind the objective lens 241 and converts an optical image into an electrical signal, and the image display unit 243 connected to the CCD 242 displays an image by converting the electrical signal into an image signal. Therefore, the diagnosis target in the body may be observed through the image.

The endoscopy unit 100 may further include an air/water supply unit 250. The air/water supply unit 250 is provided on the probe 130, and may spray air or water to the diagnosis target. The air/water supply unit 250 includes an air/water nozzle 252 which is connected to an air/water pump 251 and sprays air or water.

The air/water pump 251 supplies air or water from the outside, and the air/water nozzle 252 is connected to the air/water pump 251 through a tube (not illustrated), and provided on the probe 130, and the air/water nozzle 252 sprays air or water, which is supplied from the air/water pump 251, to the diagnosis target, thereby flushing the diagnosis target.

The endoscopy unit 100 may further include an aspiration unit 260. The aspiration unit 260 includes an aspiration pump 261, and a removal/aspiration channel 262 which is provided in the probe 130. The aspiration pump 261 is connected to the removal/aspiration channel 262, and aspirates tissues removed from the diagnosis target or aspirates substances at the periphery of the diagnosis target, thereby discharging the tissues and the substances to the outside of the body.

The removal/aspiration channel 262 provides a passageway through which the removed tissues or the substances at the periphery of the diagnosis target may be discharged to the outside. Therefore, the periphery of the diagnosis target may be cleaned.

One side of the controller 140 is connected to various types of constituent elements of the laser-induced breakdown spectroscopy endoscope, and the other side is connected to external devices (constitute elements illustrated at the right side based on the controller in FIG. 3), so that the controller 140 adjusts and controls the constituent elements.

For example, the medical diagnostic device according to the exemplary embodiment may determine whether a diagnosis target tissue has cancer while performing surgery in real time without performing a separate biopsy requiring a long period of time, and may minimize an excision site by emitting a laser to a wide tissue region and analyzing element components, to calculate an accurate lesion region.

That is, the medical diagnostic device according to the exemplary embodiment may determine in real time whether the diagnosis target has cancer by approaching the diagnosis target, which the endoscope in the related art may approach, emitting the laser directly to a portion which appears to have a malignant disease, and performing spectroscopy, while directly observing the diagnosis target, without performing a laparotomy on a patient. Based on the determination, an exact excision site and whether to excise cancer tissue may be easily determined.

The medical diagnostic device according to the exemplary embodiment is configured to be appropriately used when the diagnosis target is positioned in the body. However, the diagnosis target may be positioned at the exterior of the body. Even in this case, a medical diagnostic device according to another exemplary embodiment of the present invention may be used.

The medical diagnostic device according to another exemplary embodiment of the present invention selectively may not have the insertion tube and the bending member of the medical diagnostic device according to the aforementioned exemplary embodiment.

Referring to FIGS. 3 and 5, the medical diagnostic device according to another exemplary embodiment includes the laser guide bundle 210 which is connected to the laser head 211, the spectroscopy guide bundle 220 which is connected to the spectrophotometer 221, and the probe 130 which is provided with the laser guide bundle 210 and the spectroscopy guide bundle 220.

In addition, the medical diagnostic device further includes the light guide bundle 230 and the image capturing unit 240. The light guide bundle 230 widely spreads light transmitted from the light source 231 through the third optical fiber 232, thereby ensuring wide visibility. The mage capturing unit 240 captures an image of the diagnosis target through the objective lens 241, and transmits the image to the CCD 242 attached immediately behind the objective lens 241, thereby enabling the image display unit 243 to display the image.

The medical diagnostic device according to another exemplary embodiment is formed as an optical probe or a light guiding arm in the form of an arm so as to have convenient mobility and operational characteristics, and may analyze elements of the diagnosis target in real time in a case in which the diagnosis target is positioned at the exterior of the body. That is, even in a case in which the diagnosis target is cancer tissue, the medical diagnostic device according to another exemplary embodiment may determine whether the diagnosis target is normal or has a particular cancer, by analyzing the constituent element of the cancer tissue in real time, and comparing ratios of the s constituent elements with those of constituent elements of normal tissue and various types of cancer tissue.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

INDUSTRIAL APPLICABILITY

According to the exemplary embodiment of the present invention, it is possible to increase intensity of plasma generated on the target specimen or extend duration time of the plasma, and as a result, it is possible to increase a detection limit for each element of the target specimen by using the spectrophotometer.

In addition, according to the exemplary embodiment of the present invention, it is possible to analyze the constituent elements of the diagnosis target in real time by receiving in real time the plasma signal generated from the diagnosis target.

The invention claimed is:

1. A medical diagnostic device comprising:
 a laser-induced breakdown spectroscopy unit which includes a laser guide bundle that is connected to a laser head so as to emit a laser beam to a diagnosis target, and a spectroscopy guide bundle that is connected to a spectrophotometer so as to receive a plasma signal generated from the diagnosis target; and
 a probe which is provided with the laser guide bundle and the spectroscopy guide bundle, and disposed to approach the diagnosis target,
 wherein the laser beam is a femtosecond pulse laser beam,
 wherein the laser guide bundle includes:
 a first optical fiber which is connected to the laser head;
 a focusing lens which is disposed at an end portion of the first optical fiber on the probe so as to focus the laser beam, which is transmitted to the first optical fiber, on the diagnosis target to strike the diagnostic target to generate a plasma; and
 an endoscopy unit which includes an insertion tube that approaches the diagnosis target, a bending member that is provided at one side of the insertion tube and connects the insertion tube and the probe, and a controller which is provided at another side of the insertion tube,
 wherein the bending member is adapted to bend at 90 degrees or greater in all directions, and
 wherein the spectroscopy guide bundle includes:
 a second optical fiber which is connected to the spectrophotometer; and
 a collection lens which is disposed at an end portion of the second optical fiber on the probe so as to receive the plasma signal generated from the diagnosis target, and send the plasma signal to the second optical fiber, the plasma signal of the plasma generated from the diagnosis target by striking the diagnosis target with the laser beam focused on the diagnosis target.

2. The medical diagnostic device of claim 1, wherein:
 the focusing lens and the collection lens are disposed to be coplanar with each other at an end portion of the probe.

3. The medical diagnostic device of claim 1, further comprising:
 a plasma reactor unit which amplifies the plasma signal, which is generated from the diagnosis target, by controlling electron density and electron energy of the plasma signal,
 wherein the plasma signal amplified by the plasma reactor unit is transmitted to the spectroscopy guide bundle.

4. The medical diagnostic device of claim 1, wherein:
the endoscopy unit further includes a light guide bundle, and
the light guide bundle includes:
a third optical fiber which is connected to a light source; and
a lens which is provided on the probe at an end of the third optical fiber.

5. The medical diagnostic device of claim 1, wherein:
the endoscopy unit further includes an image capturing unit, and
the image capturing unit includes:
an objective lens which is provided on the probe and captures an image of the diagnosis target;
a charge-coupled device (CCD) which is disposed at the rear of the objective lens, and digitalizes the image; and
an image display unit which is connected to the charge-coupled device and implements an image with the digital signal.

6. The medical diagnostic device of claim 1, wherein:
the endoscopy unit further includes an air/water supply unit, and
the air/water supply unit includes:
an air/water nozzle which is provided on the probe, and sprays air or water to the diagnosis target; and
an air/water pump which is connected to the air/water nozzle, and supplies air or water from the outside.

7. The medical diagnostic device of claim 1, wherein:
the endoscopy unit further includes an aspiration unit, and
the aspiration unit includes:
a removal/aspiration channel which is provided in the probe so as to remove a tissue of the diagnosis target, or disposed at the periphery of the diagnosis target; and
an aspiration pump which is connected to the removal/aspiration channel, and aspirates the removed tissue or substances at the periphery of the diagnosis target.

* * * * *